United States Patent
Scates et al.

(10) Patent No.: US 6,657,078 B2
(45) Date of Patent: Dec. 2, 2003

(54) LOW ENERGY CARBONYLATION PROCESS

(75) Inventors: Mark O. Scates, Friendswood, TX (US); George A. Blay, Corpus Christi, TX (US); G. Paull Torrence, Corpus Christi, TX (US); Jerry A. Broussard, Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 118 days.

(21) Appl. No.: 09/778,663

(22) Filed: Feb. 7, 2001

(65) Prior Publication Data

US 2002/0151746 A1 Oct. 17, 2002

(51) Int. Cl.[7] .......................... C07C 51/12; C07C 51/42
(52) U.S. Cl. ....................................... 562/519; 562/608
(58) Field of Search .................................. 562/519, 608

(56) References Cited

U.S. PATENT DOCUMENTS

| | | |
|---|---|---|
| 3,328,449 A | 6/1967 | Haluska |
| 3,769,329 A | 10/1973 | Paulik et al. ............ 260/488 K |
| 4,139,688 A | 2/1979 | Dixon ......................... 526/41 |
| 4,552,700 A | 11/1985 | Panster et al. ................. 556/9 |
| 4,615,806 A * | 10/1986 | Hilton |
| 4,652,280 A | 3/1987 | Boeren et al. ................. 55/67 |
| 4,786,699 A | 11/1988 | Nuber et al. ................ 526/229 |
| 5,001,259 A | 3/1991 | Smith et al. ................ 562/519 |
| 5,026,908 A | 6/1991 | Smith et al. ................ 562/519 |
| 5,105,026 A | 4/1992 | Powell et al. ............... 568/727 |
| 5,139,981 A | 8/1992 | Kurland ....................... 502/11 |
| 5,144,068 A | 9/1992 | Smith et al. ................ 562/519 |
| 5,220,058 A | 6/1993 | Fish et al. .................. 562/608 |
| 5,227,524 A | 7/1993 | Jones ......................... 562/608 |
| 5,286,826 A | 2/1994 | Shih et al. .................. 526/264 |
| 5,315,042 A | 5/1994 | Cipullo et al. .............. 568/727 |
| 5,334,755 A | 8/1994 | Yoneda et al. .............. 562/519 |
| 5,416,237 A | 5/1995 | Aubigne et al. ............. 562/519 |
| 5,464,559 A | 11/1995 | Marchin et al. ............. 252/181 |
| 5,466,874 A | 11/1995 | Scates et al. ................ 562/519 |
| 5,504,234 A | 4/1996 | Omura et al. ................ 556/439 |
| 5,576,458 A * | 11/1996 | Minami et al. |
| 5,625,095 A | 4/1997 | Miura et al. ................. 562/519 |
| 5,801,279 A | 9/1998 | Miura et al. ................. 562/608 |
| 5,962,735 A | 10/1999 | Kulprathipanja et al. ... 562/608 |
| 6,066,762 A * | 5/2000 | Yoneda et al. |

FOREIGN PATENT DOCUMENTS

| | | | |
|---|---|---|---|
| EP | 0482787 A2 | 4/1992 | .......... C07C/51/47 |
| EP | 0685445 A1 | 12/1995 | .......... C07C/53/08 |
| GB | 2112394 A | 7/1983 | .......... C07C/51/47 |
| WO | WO98/17619 | 4/1998 | .......... C07C/51/00 |

OTHER PUBLICATIONS

"The Cativa ™ Process for the Production of Acetic Acid", Chem. Ind. (Dekker) 1998, 75 Catalysis of Organic Reactions of Derrick J. Watson, pp. 369–380.

* cited by examiner

Primary Examiner—Johann Richter
Assistant Examiner—Paul A. Zucker
(74) Attorney, Agent, or Firm—James J. Mullen

(57) ABSTRACT

A low energy process for producing acetic acid by the carbonylation of methanol is disclosed. The process involves a rhodium-catalyzed system operated at less than about 14% water utilizing up to 2 distillation columns. The process is preferably controlled such that the product stream has a low level of propionic acid impurity and the level of aldehyde impurities is minimized by way of aldehyde removal or minimizing aldehyde generation. The level of iodides is controlled by contacting the product, at elevated temperatures, with ion exchange resins. In preferred embodiments, at least one silver or mercury exchanged macroreticular strong acid ion exchange resin is used to purify the product. The high temperature treatment provides the added benefit of controlling the Color Value (Pt—Co units) of the product stream.

28 Claims, 5 Drawing Sheets

REMOVAL OF NEOPENTYL IODIDE AT 25°C
COMPARISON WITH HEXYL IODIDE

ELUTION ISOTHERMS FOR DODECYL IODIDE

LOW ENERGY CARBONYLATION PROCESS

TECHNICAL FIELD

The present invention relates generally to processes for making acetic acid; and in particular to a low energy process for making acetic acid by way of carbonylating methanol with carbon monoxide and utilizing at most two distillation columns in the primary purification train

BACKGROUND ART

Among currently employed processes for synthesizing acetic acid, one of the most useful commercially is the rhodium catalyzed carbonylation of methanol with carbon monoxide as taught in U.S. Pat. No. 3,769,329 of Paulik et al. The carbonylation catalyst comprises rhodium, either dissolved or otherwise dispersed in a liquid reaction medium along with a halogen containing catalyst promotor as exemplified by methyl iodide. Generally, the reaction is conducted with the catalyst being dissolved in a liquid reaction medium through which carbon monoxide gas is continuously bubbled. Paulik et al. disclosed that water may be added to the reaction mixture to exert a beneficial effect upon the reaction rate. Water concentrations greater than about 14 weight percent are typically used. This is the so called "high water" carbonylation process.

An alternative to the "high water" carbonylation process is the "low water" carbonylation process as disclosed in U.S. Pat. Nos. 5,001,259; 5,026,908; and 5,144,068. Water concentrations below 14 weight percent and even below 10 weight percent can be used in the "low water" carbonylation process. Employing a low water concentration simplifies downstream processing of the desired carboxylic acid to its glacial form.

It is desirable in a carbonylation process for making acetic acid to minimize the number of distillation operations in order to minimize energy usage in the process. In this respect there is disclosed in U.S. Pat. No. 5,416,237 to Aubigne et al. a process for the production of acetic acid by carbonylation of methanol in the presence of a rhodium catalyst, methyl iodide, and an iodide salt stabilizer. The improvement according to the '237 patent resides in maintaining a finite concentration of water up to about 10 percent by weight and a methyl acetate concentration of at least 2 percent by weight in the liquid reaction composition and recovering the acetic acid product by passing the liquid reaction composition through a flash zone to produce a vapor fraction which is passed to a single distillation column from which the acetic acid product is removed. The drawback of eliminating distillation stages is that the level of purity of the product suffers. In particular the distillation columns tend to remove high boiling iodides as well as aldehyde contamination products. Both of these impurities impact the commercial desirability of the final product.

Various means for removing iodides are well known in the art. It was discovered by Hilton that macroreticulated, strong acid cationic exchange resins with at least one percent of their active sites converted to the silver or mercury form exhibited remarkable removal efficiency for iodide contaminants in acetic acid or other organic media. The amount of silver or mercury associated with the resin may be from as low as about one percent of the active sites to as high as 100 percent. Preferably about 25 percent to about 75 percent of the active sites were converted to the silver or mercury form and most preferably about 50 percent. The subject process is disclosed in U.S. Pat. No. 4,615,806 for removing various iodides from acetic acid. In particular there is shown in the examples removal of methyl iodide, HI, $I_2$ and hexyl iodide.

Various embodiments of the basic invention disclosed in U.S. Pat. No. 4,615,806 have subsequently appeared in the literature. There is shown in U.S. Pat. No. 5,139,981 to Kurland a method for removing iodides from liquid carboxylic acid contaminated with a halide impurity by contacting the liquid halide contaminant acid with a silver (I) exchanged macroreticular resin. The halide reacts with the resin bound silver and is removed from the carboxylic acid stream. The invention in the '981 patent more particularly relates to an improved method for producing the silver exchanged macroreticular resins suitable for use in iodide removal from acetic acid.

U.S. Pat. No. 5,227,524 to Jones discloses a process for removing iodides using a particular silver-exchanged macroreticular strong acid ion exchange resin. The resin has from about 4 to about 12 percent cross-linking, a surface area in the proton exchanged form of less than 10 $m^2/g$ after drying from the water wet state and a surface area of greater than 10 $m^2/g$ after drying from a wet state in which the water has been replaced by methanol. The resin has at least one percent of its active sites converted to the silver form and preferably from about 30 to about 70 percent of its active sites converted to the silver form.

U.S. Pat. No. 5,801,279 to Miura et al. discloses a method of operating a silver exchanged macroreticular strong acid ion exchange resin bed for removing iodides from a Monsanto type acetic acid stream. The operating method involves operating the bed silver-exchanged resin while elevating the temperatures in stages and contacting the acetic acid and/or acetic anhydride containing the iodide compounds with the resin. Exemplified in the patent is the removal of hexyl iodide from acetic acid at temperatures of from about 25° C. to about 45° C.

So also, other ion exchange resins have been used to remove iodide impurities from acetic acid and/or acetic anhydride. There is disclosed in U.S. Pat. No. 5,220,058 to Fish et al. the use of ion exchange resins having metal exchanged thiol functional groups for removing iodide impurities from acetic acid and/or acetic anhydride. Typically, the thiol functionality of the ion exchange resin has been exchanged with silver, palladium, or mercury.

There is further disclosed in European Publication No. 0 685 445 A1 a process for removing iodide compounds from acetic acid. The process involves contacting an iodide containing acetic acid stream with a polyvinylpyridine at elevated temperatures to remove the iodides. Typically, the acetic acid was fed to the resin bed according to the '445 publication at a temperature of about 100° C.

With ever increasing cost pressures and higher energy prices, there has been ever increasing motivation to simplify chemical manufacturing operations and particularly to reduce the number of manufacturing steps. In this regard, it is noted that in U.S. Pat. No. 5,416,237 to Aubigne et al. there is disclosed a single zone distillation process for making acetic acid. Such process modifications, while desirable in terms of energy costs, tend to place increasing demands on the purification train. In particular, fewer recycles tend to introduce (or fail to remove) a higher level of iodides into the product stream and particularly more iodides of a higher molecular weight. For example, octyl iodide, decyl iodide and dodecyl iodides may all be present in the product stream as well as hexadecyl iodide; all of which are difficult to remove by conventional techniques.

Other impurities in acetic acid made by way of the rhodium catalyzed carbonylation of methanol, notably aldehydes and propionic acid, are likewise known. It is proposed in an article by Watson, *The Cativa™ Process for the Production of Acetic Acid*, Chem. Ind. (Dekker) (1998) 75 Catalysis of Organic Reactions, pp. 369–380, that acetaldehyde undergoes reduction by hydrogen in the rhodium-catalyzed system to give ethanol which subsequently yields propionic acid. It is postulated that enhanced rhodium catalyzed systems have increased standing levels of rhodium-acyl species which will form free acetaldehydes at a higher rate.

The precise chemical pathway within the methanol carbonylation process that leads to the production of crotonaldehyde, 2-ethyl crotonaldehyde and other permanganate reducing compounds is not well understood. One prominent theory for the formation of the crotonaldehyde and 2-ethyl crotonaldehyde impurities in the methanol carbonylation process is that they result from aldol and cross-aldol condensation reactions that involve acetaldehyde. Substantial efforts have been directed to removing acetaldehyde.

Conventional techniques used to remove acetaldehyde and other carbonyl impurities have included treatment of acetic acid with oxidizers, ozone, water, methanol, amines, and the like. In addition, each of these techniques may or may not be combined with the distillation of the acetic acid. The most typical purification treatment involves a series of distillations of the product acetic acid. Likewise, it is known that carbonyl impurities can be removed from organic streams by treating the organic streams with an amine compound such as hydroxyl amine which reacts with the carbonyl compounds to form oximes followed by distillation to separate the purified organic product from the oxime reaction products. However, this method of treating the product acetic acid adds cost to the process.

There is disclosed in U.S. Pat. No. 5,625,095 to Miura et al. and PCT International Application No. PCT/US97/1871 1, Publication No. WO 98/17619 various methods of removing acetaldehydes and other impurities from a rhodium-catalyzed acetic acid production process. Generally, these methods involve removing undesirable impurities from recycle streams to reduce acetaldehyde concentrations in the system.

SUMMARY OF INVENTION

There is provided in accordance with the present invention a low energy carbonylation process utilizing in the primary purification train at most two distillation columns. In accordance with the inventive process, the amount of aldehydes in the product stream is preferably controlled by removal of aldehydes from the system or by operating the process such that low levels of aldehyde contaminants and their derivatives, such as organic iodides are generated. Moreover, high boiling iodides are removed by way of a high temperature ion exchange resin such that the product exhibits high levels of purity.

More specifically, there is provided in accordance with the present invention a continuous process for producing acetic acid including:

(a) reacting methanol with a carbon monoxide feed stock in a carbonylation reactor holding a catalytic reaction medium while maintaining in said reaction medium during the course of said reaction at least a finite concentration of from about 0.1 weight percent up to less than 14 weight percent of water together with: (i) a salt soluble in the reaction medium at the reaction temperature in an amount operative to maintain a concentration of ionic iodide in the range of from about 2 to about 20 weight percent effective as a catalyst stabilizer and co-promoter; (ii) from about 1 to about 20 percent methyl iodide; (iii) from about 0.5 to about 30 weight percent methyl acetate; (iv) a rhodium catalyst; and (v) acetic acid. A portion of the reaction medium is withdrawn from the reactor and vaporized in a flashing step. The flashed vapor is distilled to form a liquid acetic acid product stream utilizing up to two distillation columns while providing one or more recycle streams to the reactor. The amount of aldehyde in the liquid acetic acid product stream is optionally controlled by one of three techniques or combinations of these techniques which include: (i) operating the reactor at a total pressure of from about 15 to about 40 atmospheres while maintaining a partial pressure of hydrogen of less than about 6 psia; (ii) maintaining in the reaction medium a concentration of less than about 5 weight percent methyl iodide; and (iii) removing aldehyde impurities from at least one of the recycle streams.

Particularly preferred iodide salts are alkali metal iodide salts such as lithium iodide. The salts may be formed in-situ, for example, by adding lithium acetate or salt forming phosphines including pentavalent phosphine oxides to the reactor. So long as the ionic iodide is measurable by silver titration, minimizes rhodium precipitation and operates to maintain the majority of or at least 50% of the rhodium in the Rh(I) oxidation state at water concentrations of less than 14%, it is a "salt", as defined herein. Salts may be used alone or in combination to maintain the requisite level of ionic iodide. Compare, U.S. Pat. No. 5,817,869 with U.S. Pat. No. 6,031,129, the disclosures of which are incorporated by reference.

Iodides are removed from the liquid acetic acid product residue stream such that the product has an iodide content of less than about 10 ppb iodide. The iodides are removed by one of two processes:

(a) a first process involves contacting the liquid acetic acid product residue stream with an anionic ion exchange resin at a temperature of at least about 100° C. followed by contacting the liquid acetic acid product residue stream with a silver or mercury exchanged ion exchange substrate wherein at least one percent of the active sites (i.e., sulfonic acid moieties) of the resin have been converted to the silver or mercury form;

(b) a second process involves contacting the liquid acetic acid product residue stream with a silver or mercury exchanged ion exchange substrate at a temperature of at least about 50° C. wherein at least one percent of the active sites of the resin have been converted to the silver or mercury form.

When utilizing an anionic resin, particularly preferred resins include polyvinylpyridine resins and polyvinylpyrrolidone resins. The anionic resins are typically employed at a temperature of at least about 150° C.

When a silver or mercury exchanged substrate is used, it is typically a macroreticular, strong acid cationic resin. Temperatures may be from about 60 to about 100° C. A minimum temperature of 60° C. is sometimes employed while a minimum temperature of about 70° C. may likewise be preferred in some embodiments.

In general, when a silver or mercury exchanged strong acid cationic resin is employed typically from about 25% to about 75% of the active sites are converted to the silver or mercury form. Most typically about 50% of the active sites are so converted.

The aldehydes in the system may optionally be controlled by removing aldehydes from the recycle to the reactor by way of, for example, distillation from a condensed recycle stream.

Alternatively the level of aldehyde impurities in the system may be controlled by minimizing the partial pressure of hydrogen or the levels of methyl iodide in the reactor. In particular, at a total pressure in the reactor of 15 to 40 atmospheres absolute a partial pressure of from about 0.1 to about 4 psia of hydrogen may be employed. A partial pressure of hydrogen of from about 1 to about 4 psia may be preferred. Relatively low level of methyl iodide in the reactor may be about 5 weight percent or less. A level of methyl iodide of from about 1 to about 5 weight percent may likewise be employed.

In another aspect of the invention, there is provided an acetic acid made by the process described herein, wherein the product has a propionic acid content of less than about 500 ppm. Typically, the product acid has a propionic acid content of less than about 250 ppm, with less than about 150 ppm being preferred.

Particularly preferred processes are those utilizing a silver-exchanged cationic substrate for removing iodides and relatively low hydrogen partial pressures in the reactor for controlling aldehyde impurities. The product stream in many cases includes organic iodides with a C10 or more aliphatic chain length which need to be removed. Sometimes more than 25% of the iodides present, or even 50%, have an organic chain length of more than 10 carbon atoms.

Decyl iodides and dodecyl iodides are especially prevalent in the absence of heavy ends and other finishing apparatus and are difficult to remove from the product stream as will be appreciated from the data hereinafter appearing. The silver-exchanged cationic substrates of the present invention typically remove over 90% of such iodides; oftentimes the product stream has from 10 to about 1000 ppb total iodide prior to treatment which would make the product unusable for iodide-sensitive applications.

From about 20 ppb to about 750 ppb prior to iodide removal treatment is somewhat typical; whereas the iodide removal treatment is preferably operative to remove at least about 99% of the total iodide present.

In a typical embodiment, iodide removal treatment involves contacting the product with a silver-exchanged sulfonic acid functionalized macroreticular ion exchange resin, wherein the product has an organic iodide content of greater than 100 ppb prior to treatment and an organic iodide contact of less than 10 ppb after contacting the resin.

The following related applications belonging to the Assignee of the present invention are incorporated herein by reference, the pertinent portions of which are further described herein:

U.S. Ser. No. 09/386,708, filed Aug. 31, 1999 of Mark O. Scates et al., entitled "Rhodium/Inorganic Iodide Catalyst System for Methanol Carbonylation Process with Improved Impurity Profile"; U.S. Ser. No. 09/386,561, filed Aug. 31, 1999 of Hung-Cheun Cheung et al., entitled "Rhodium/Inorganic Iodide Catalyst System for Methanol Carbonylation Process with Improved Impurity Profile"; and U.S. Ser. No. 09/534,868, filed Mar. 21, 2000 of George A. Blay et al., entitled "Method of Removing Organic Iodides from Organic Media".

The foregoing and further features of the present invention will be further appreciated form the discussion which follows.

Unless otherwise indicated by the context or explicitly, as used herein, "%", "percent" or the like refers to weight percentage. Likewise, the terminology "ppm", "parts per million" and the like and "ppb" refers to parts per million by weight or parts per billion by weight, respectively, unless otherwise defined. The terminology "active sites" of an ion exchange resin refers to the ion exchange sites available in such a resin. For example, in a cationic ion exchange resin having a cation exchange capacity of 2 meq/g, 2 meq/g constitutes 100% of the active sites, 1 meq/g constitutes 50% of the active sites and so forth.

DESCRIPTION OF DRAWINGS

The invention is described in detail below in connection with the various Figures. In the Figures.

DETAILED DESCRIPTION

Figure 1:
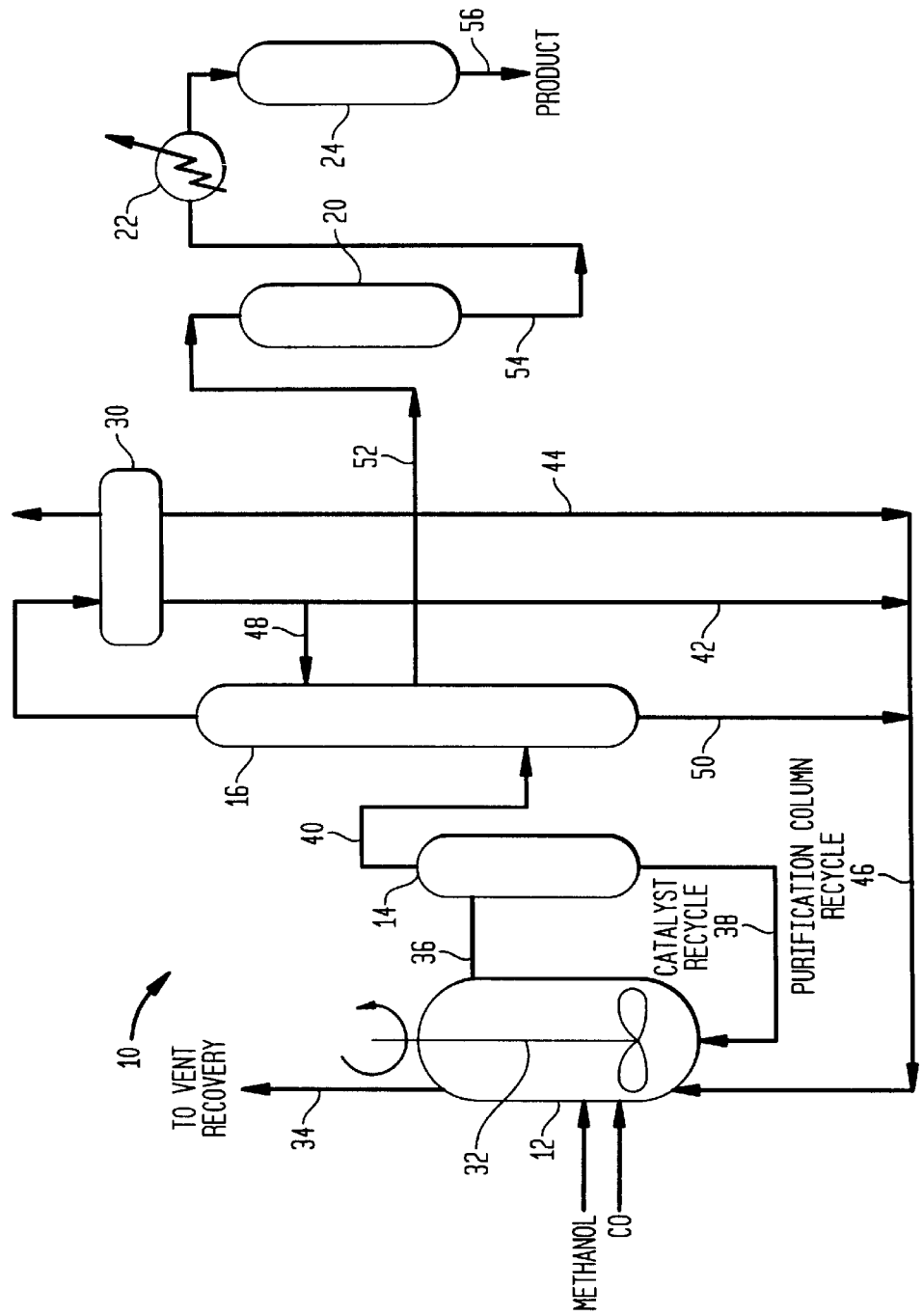
FIG. 1 is a schematic diagram of a first apparatus useful for practicing the present invention.

It will be appreciated that the rhodium catalyzed process for preparing acetic acid is well known. Thus, the invention will be described in terms of differences from prior art processes such as are described in U.S. Pat. Nos. 5,001,259; 5,026,908; 5,144,068, the disclosures of which are hereby incorporated by reference. There are two criteria which are desirably satisfied to maintain optimum performance of reaction system for the rhodium catalyzed carbonylation of methanol to acetic acid. This is over and above the maintenance of a stable catalyst system from which the rhodium catalyst does not precipitate during the course of product recovery. First it is desired to maintain a high productivity in the carbonylation reactor itself as measured by the quantity of acetic acid formed per unit time per unit volume or weight of liquid reaction medium contained in the reactor. This might be termed "reactor productivity" or "reactor space time yield", also referred to as "STY". Second, the present process improvement contemplates the maintenance of optimal productivity as measured by the ultimately-recovered glacial acetic acid in the combined system including both the carbonylation reactor and the purification train. It will be recognized by one skilled in the art that water is an undesirable component of the crude acetic acid and that the more water there is in the product stream the greater will be the operating cost and required capital investment in the product recovery purification system. Thus, there is also a system productivity to be considered in addition to the reaction productivity with the system productivity depending upon the degree to which water is kept out of the residue of the crude product stream. The drier this stream is, the higher will be the overall system productivity so long as the reaction productivity is maintained with a suitable impurity profile.

For purposes of this invention, the catalyst which is employed includes a rhodium component and a halogen promotor in which the halogen is typically iodine. The catalyst system is preferably generally homogenous as is well known. The rhodium component of a catalyst system of the present invention is believed to be present in the form of a coordination compound of rhodium with a halogen component providing at least one of the ligands of such coordination compound. In addition to the coordination of rhodium and halogen, it is believed that carbon monoxide and ligands form coordination compounds or complexes with rhodium. The rhodium component of the catalyst system in the present invention may be provided by introducing into the reaction zone rhodium in the form of rhodium metal, rhodium salts and oxides, organic rhodium compounds, coordination compounds of rhodium and the like. The halogen promoting component of the system consists of a halogen compound comprising an organic halide. Thus alkyl, aryl and substituted alkyl or aryl halides can be used. Preferably, the halide promotors are present in the form of an alkyl halide in which the alkyl radical corresponds to the alkyl radical of the free alcohol which is carbonylated. For example in the carbonylation of methanol to acetic acid, the halide promotor will comprise methyl halide and most preferably methyl iodide. The reaction medium employed may include any solvent compatible with the catalyst system and may include pure alcohols, or mixtures of the alcohol feed stock and/or the desired carboxylic acid and/or esters of the two compounds. The preferred solvent and reaction medium for the process of this invention comprises acetic acid.

Water is also maintained in the reaction medium but at relatively low concentrations; that is concentrations below about 14%. It has been shown (U.S. Pat. Nos. 5,001,259; 5,026,908; and 5,144,068) that reaction rate substantially equal to and above reaction rates obtained with water concentrations above about 14% can be achieved with water concentrations below 14% and as low as 0.1 weight percent. In accordance with the present invention the desired reaction rates are obtained at low water concentrations by maintaining in the reaction medium an ester which corresponds to the alcohol being carbonylated and the acid product of the carbonylation reactant and most preferably an additional iodide ion which is over and above the iodide which is present as a catalyst promotor such as methyl iodide or other organic iodide. Thus, in the carbonylation reaction of methanol to acetic acid, the ester is methyl acetate and the additional iodide co-promotor is an iodide salt with lithium iodide being most preferred.

It has been found that under low water concentrations, methyl acetate and iodide ion act as rate promoters when relatively high concentrations of each of these components are present and that the promotion is higher when both of these components are present simultaneously as disclosed in U.S. Pat. Nos. 5,001,259; 5,026,908; 5,144,068.

Additionally, it has been shown that in reaction mediums having a methyl acetate concentration of greater than about 2 weight percent, iodide ion is necessary not only to increase the reaction rate but also to stabilize the rhodium catalyst due to the deleterious effect of high methyl acetate concentrations on its stability, even at high water concentrations.

Table 1 gives suitable ranges of some of the various reactor components used in the process of the present invention.

TABLE 1

Broad and preferred ranges of Components.

| | STABILIZATION | | RATE ENHANCEMENT | |
| --- | --- | --- | --- | --- |
| | Broad wt % | Preferred wt % | Broad wt % | Preferred wt % |
| Water | 0.1–14 | 1–10 | 0.1–14 | 1–10 |
| Inorganic Iodide | 2–20 | 5–15 | 2–20 | 10–20 |
| Methyl Acetate | 0.5–30 | 0.5–5 | 0.5–30 | 2–5 |
| Methyl iodide | 1–20 | 2–16 | 1–20 | 5–16 |
| Acetic Acid | balance | balance | balance | balance |
| Rhodium (ppm) | 500–5000 | 750–1500 | 500–5000 | 750–1500 |

Amounts of water, iodide ion, methyl acetate and methyl iodide are set forth as both a broad range and a preferred, or optimal ranges for obtaining both catalyst stabilization and reaction rate enhancement. The preferred range is that which is preferred from the standpoint of optimal performance of the entire system including the primary product recovery system as explained above. It will be seen that the recommended concentrations are, very generally, the same for both stabilization and also rate enhancement.

Suitably stable ion exchange resins utilized in connection with the present invention for preparing silver or mercury-exchanged resins for iodide removal typically are of the "$RSO_3H$" type classified as "strong acid", that is, sulfonic acid, cation exchange resins of the macroreticular (macroporous) type. Particularly suitable ion exchange substrates include Amberlyst® 15 resin (Rohm and Haas) suitable for use at elevated temperatures. Other stable ion exchange substrates such as zeolites may be employed, provided that the material is stable in the organic medium at the conditions of interest, that is, will not chemically decompose or release silver or mercury into the organic medium in unacceptable amounts. Zeolite cationic ion exchange substrates are disclosed for example, in U.S. Pat. No. 5,962,735 to Kulprathipanja et al., the disclosure of which is incorporated herein by reference.

At temperatures greater than about 50° C., the silver or mercury exchanged cationic substrate may tend to release small amounts of silver on the order of 500 ppb or less and thus the silver or mercury exchanged substrate is chemically stable under the conditions of interest. More preferably silver losses are less than about 100 ppb into the organic medium and still more preferably less than about 20 ppb into the organic medium. Silver losses may be slightly higher upon start up or if the process is conducted with exposure to light since silver iodide is believed photoreactive and may form soluble complexes if contacted by light. In any event, if so desired, a bed of cationic material in the unexchanged form may be placed downstream of the silver or mercury exchange material of the present invention, to catch any silver or mercury released from the cationic ion exchange resin.

The process of the present invention may be carried out in any suitable configuration. A particularly preferred configuration is to utilize a bed of particulate material (termed herein a "guard bed") inasmuch as this configuration is particularly convenient. A typical flow rate, such as is used when acetic acid is to be purified, is from about 0.5 to about 20 bed volumes per hour (BV/hr). A bed volume is simply the volume occupied by the resin in the bed. Simply put, for 100 ml of resin the bed volume is said to be 100 ml. Typical flow rates are usually from about 6 to about 10 BV/hr, with about 8 BV/hr being preferred in many embodiments.

Similar flow rates are employed when utilizing an anionic guard bed of a pyridine or pyrrolidone resin. The terminology "pyridine resin", "pyridine ring-containing polymer", "pyridine polymer" and the like used herein is intended to refer to a polymer containing substituted or non-substituted pyridine rings or substituted or non-substituted, pyridine-containing polycondensed rings such as quinoline rings. The substituents include those inert to the methanol carbonylation process conditions such as an alkyl group and alkoxy group. Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and divinylbenzene, copolymers of styrene, vinylbenzene and divinylbenzene, copolymers of vinylmethylpyridine and divinylbenzene and copolymers of vinylpyridine, methyl acrylate and ethyl diacrylate. Particularly preferred polymers are described in U.S. Pat. No. 5,334,755 to Yoneda et al., the disclosure of which is incorporated herein by reference. Relatively high degrees of crosslinking in the polymer is most preferred.

The terminology "pyrrolidone resin", "pyrrolidone ring-containing polymer", pyrrolidone polymer and the like used herein is intended to refer to a polymer containing substituted or non-substituted pyrrolidone rings. The substituents may include those inert to the methanol carbonylation medium such as alkyl groups or alkoxy groups. Typical examples of insoluble, pyrrolidone ring-containing polymer include those obtained by reaction of vinyl pyrrolidone with a di-vinyl monomer-containing vinyl monomer such as a co-polymer of a vinyl pyrrolidone and divinyl benzene. Pyrrolidone polymers are discussed in U.S. Pat. No. 5,466,874 of Scates et al. as well as U.S. Pat. Nos. 5,286,826; 4,786,699 and 4,139,688, the disclosures of which are incorporated herein by reference. A preferred pyrrolidone polymer substrate is available under the trade name of Reillex® from Reilley Tar and Chemical Corporation of Indianapolis, IND.

It is desirable that the above nitrogen heterocyclic ring-containing polymer should be crosslinked by at least 10%, preferably at least 15% or 20% and up to 75%. A degree of crosslinking below 10% is disadvantageous because the mechanical strength of the polymer may degrade during use. As the degree of crosslinking increases, the availability of the polymer surface may be unduly restricted. A maximum degree of crosslinking of 50 or 60 percent is then preferred. The term "degree of crosslinking" used herein is intended to refer to the content, in terms of % by weight, of the divinyl monomer, for example.

A pyridine or pyrrolidone insoluble polymer may be in the free base or N-oxide form or quaternized form as noted above. The insoluble, pyridine or pyrrolidone ring-containing polymer is preferably in a bead or granular form, more preferably in a spherical form, having a particle diameter of 0.01–2 mm, preferably 0.1–1 mm, more preferably 0.25–0.7 mm. Commercially available pyridine-containing polymers such as Reillex-425 (product of Reilly Tar and Chemical Corporation) and KEX-316, KeX-501 and KEX-212 (products of Koei Chemical Co., Ltd.) may be suitably used for the purpose of the present invention. As noted above pyrrolidones are also available from Reilly Tar and a degree of crosslinking of at least about 20% is preferred.

The present invention is further described in connection with FIGS. 1 and 2 wherein like numerals designate similar parts. There is shown in FIG. 1 a first apparatus 10 useful for practicing the process of the present invention. Apparatus 10 includes a reactor 12, a flasher, a splitter column 16, as well as optionally, a high temperature resin bed 20, heat exchanger means 22 and a resin bed 24. There is further provided a condenser 30 for collection the light ends from the splitter column. In FIG. 1, column 16 operates as both a light ends and dehydration distillation column.

Acetic acid is manufactured in a liquid phase reaction typically at about 150° C.–200° C. in reactor 12 at a pressure of from about 30 to about 60 bar. Carbon monoxide and methanol are introduced continuously into the back-mixed reactor wherein carbon monoxide mass transfer into the liquid phase is maximized with adequate mixing, indicated at 32, at a high carbon monoxide partial pressure. Non-condensable by-products are vented from the reactor to maintain an optimum carbon monoxide partial pressure in the reactor, as indicated at 34. The reactor off-gas is treated to recover reactor condensables, e.g., methyl iodide, before flaring.

Catalyst solution, containing the product acetic acid, as well as the various components of the reaction mixture, such as rhodium complexes and iodide salts, is drawn off and provided to flasher 14 by way of line 36. In flasher 14, the product acetic acid and the majority of the light ends (methyl iodide, methyl acetate, water) are separated from the reactor catalyst solution and forwarded with dissolved gasses to purification section byway of an adiabatic single stage flash. This crude separation also functions to remove the exothermal heat of reaction. The catalyst solution is recycled to reactor 12 by way of a catalyst recycle line 38.

The vapor product from flasher 14 proceeds via line 40 to splitter (light ends) column 16. Methyl iodide, methyl acetate, and a portion of the water are condensed overhead at 30 to form two phases (organic and aqueous). Either or both phases may be treated to remove aldehydes and aldehyde impurities before being returned to the reactor via lines 42, 44, 46 indicated on FIG. 1. As noted earlier, preferred methods for treating these phases are described in U.S. Pat. No. 5,625,075 and WIPO publication WO 98/17619, the disclosures of which are incorporated herein by reference. A portion of the overhead, the aqueous phase, for example, may be recycled to column 16 as reflux via line 48, whereas the residue of column 16 is recycled to reactor 12 via lines 50, 46.

Product acetic acid is withdrawn via a sidestream 52 and fed to a resin bed 20 at elevated temperature and pressure. The sidestream is located near the bottom of the column and can be withdrawn as a vapor or liquid sidestream. If it is a vapor sidestream, it is condensed prior to feeding to bed 20. Typically, bed 20 is operated at a temperature above about 170° C. and consists of an anionic, heterocyclic-ring containing polymeric ion exchange resin. Most preferably, resin bed 20 is a bed of particulate pyridine resin or pyrrolidine resin described above, suitably crosslinked so that it will withstand processing at elevated temperatures and pressures.

The product leaves high temperature resin bed 20 via line 54 and conveyed to heat exchanger 22 wherein the product is cooled to a temperature of about 100° C. or less.

A silver-exchanged cationic macroporous resin bed 24 is used to further remove iodides.

Product acetic acid leaves the system at line 56.

Figure 2:
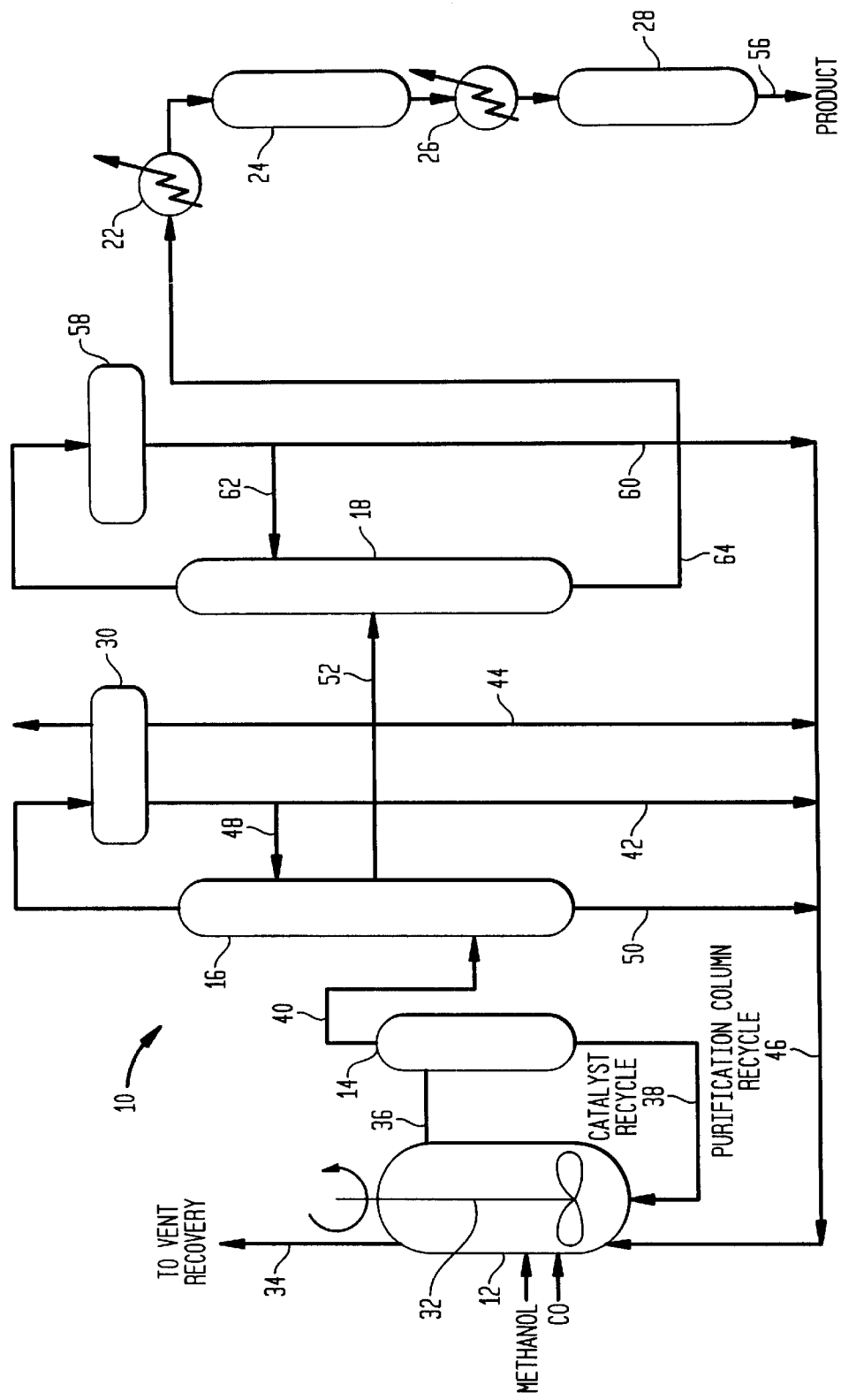
FIG. 2 is a schematic diagram of a second apparatus useful for practicing the present invention.

FIG. 2 shows an alternate apparatus 10 wherein the inventive process may be practiced. Parts are numbered in FIG. 2 as in FIG. 1 and operated in substantially the same manner, except that there is further provided a separate dehydration column 18 for receiving the product acetic acid stream from column 16 via line 52 as well as a different iodide removal system as described below. The overhead of vessel 18 is condensed at 58 and becomes two phases, aqueous and organic, both of which are recycled to reactor 12. The aqueous stream is also refluxed to column 18 via line 62. The dry crude acetic acid exits column 18 as a residue stream at 64 and is provided to heat exchanger 22 which cools the product such that the average temperature in resin bed 24 is maintained preferably between about 50 and 70°. If it is desired to operate bed 24 at a higher temperature, it may be convenient to locate heat exchanger 22 upstream of bed 24. After cooling, the stream is treated in resin bed 24 and cooled again in heat exchanger 26 before being fed to resin bed 28. Resin bed 28 is also a bed of silver or mercury exchanged cationic ion exchange media and is typically operated at an average product temperature of from about 35° C. to about 20° C.

As used herein, the terminology "primary purification train" and like terminology refers to purification equipment operating on the primary product stream from the flasher, excluding vent recovery equipment, scrubbers, alkanes removal and so forth. Thus, with respect to FIG. 1, the primary purification train consists of light ends and dehydration column 16, high temperature resin bed 20, resin bed 24 and associated conduits. Note that the flasher is not generally considered part of the primary purification train nor are scrubbers and the like. Thus with respect to FIG. 2, the primary purification train includes light ends column 16, dehydration column 18 and resin beds 24 and 28.

Particularly preferred methods of operating the resin beds, especially bed 24, is described below. Further, it is seen that aldehyde impurities are controlled by optimizing conditions in reactor 12 as hereinafter described.

EXAMPLES

The following Examples 1–5 and comparative Examples A through F used the procedures described below. Unless otherwise noted, Iodide removal was performed using silver exchanged Amberlyst® are 15 resin. The resin (100 ml wet) was loaded into a 22 mm OD glass column and acetic acid containing iodides was eluted at a flow rate of 13.3 ml/min. Iodide levels in the eluate were measured every two (2) hours. Total iodides are measured in the eluate by any suitable technique. One suitable technique is by way of neutron activation analysis (NAA) as is well known in the art. The iodide levels for particular species were also measured. A preferred method in this latter respect is gas chromatography utilizing an electron capture detector.

Comparative Examples A and B

Figure 3:
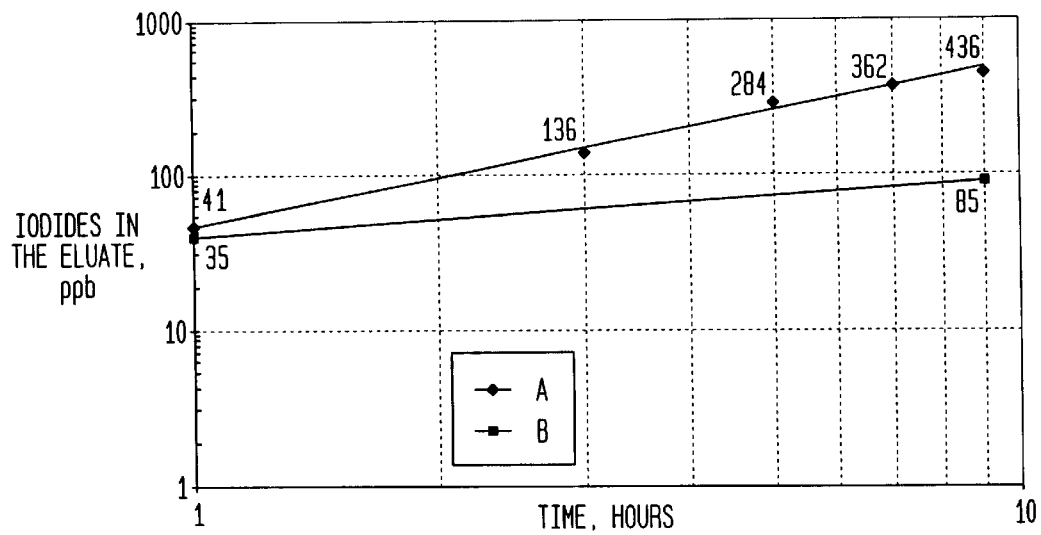
FIG. 3 is a plot of iodide concentration in treated acetic acid vs. time for commercial samples of material from the residue of a drying column wherein treatment is carried out at ambient conditions.

Samples of the residue from the drying column of a conventional Monsanto type acetic acid plant containing 540 ppb total iodide and 238 ppb total iodide were treated at room temperature using a silver exchanged bed of Amberlyst® 15 resin and the total iodides in the eluate were measured as a function of time as shown in FIG. 3. As can be seen from FIG. 3, total iodide removal was typically less than about 90% at the start of the test and progressively decayed over a ten hour time period to much lower removal efficiencies.

The various iodide components in the feed were identified to include:
methyl iodide
ethyl iodide
2-iodo-2-methyl propane
propyl iodide
2-butyl iodide
butyl iodide
iodine
pentyl iodide
hexyl iodide
octyl iodide
decyliodide
dodecyl iodide
hexadecyl iodide The predominant high molecular weight organic iodide components identified were decyl iodide and dodecyl iodide.

Comparative Examples of C and D and Example 1

Figure 4:
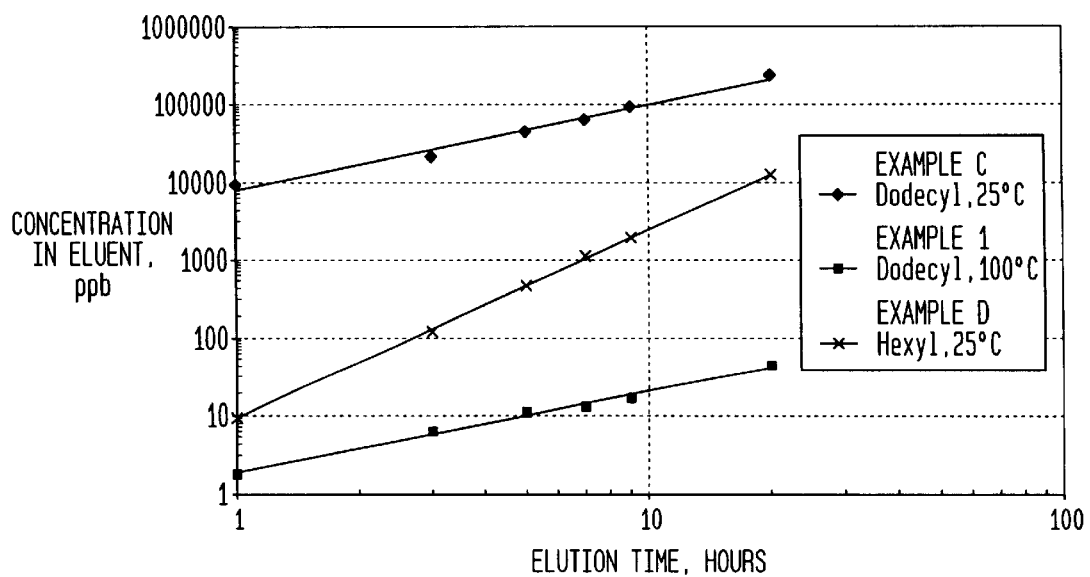
FIG. 4 is a plot of iodide in acetic acid eluent vs. time for dodecyl iodide and hexyl iodide after treatment at various temperatures.

Following the procedure outlined above, the temperature dependence of the guard bed performance was measured for relatively high (ppm) levels of organic iodides in acetic acid. Results for dodecyl iodide (Example C) and hexyl iodide (Example D) at 25° C. and for dodecyl iodide at 100° C. are shown in FIG. 4. Results indicate that guard bed performance is greatly enhanced at 100° C. over 25° C., particularly for dodecyl iodide. Performance improvements include both removal efficiency and useful life of the bed.

Comparative Examples E, F

Figure 5:
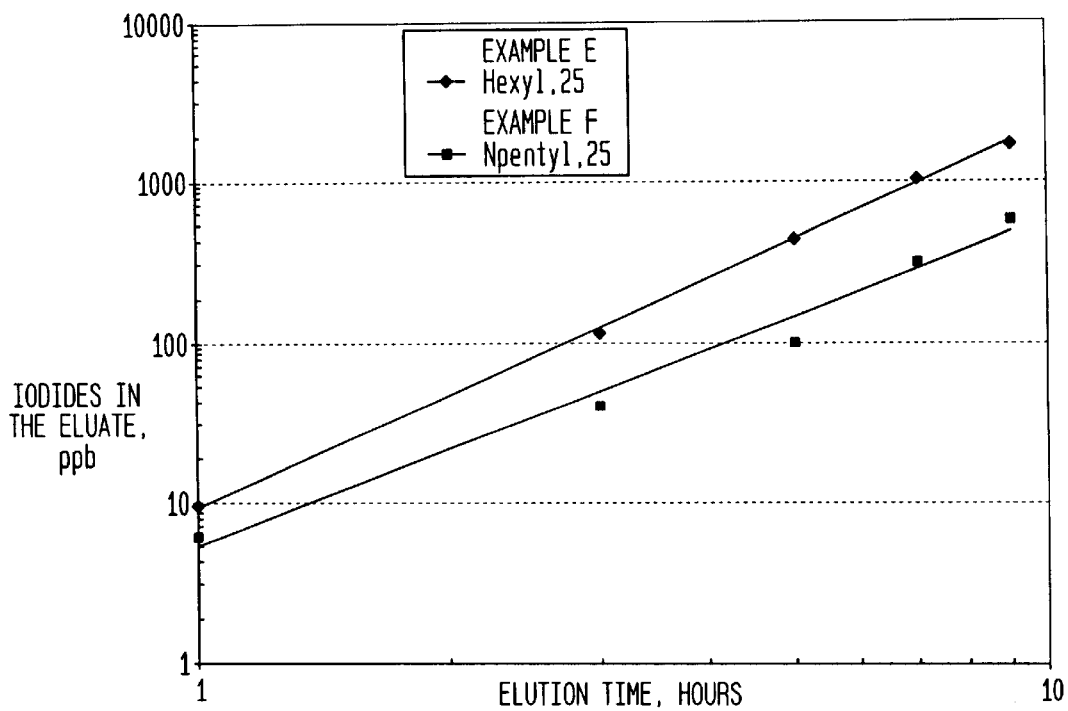
FIG. 5 is a plot of iodide vs. time in acetic acid eluent after treatment for hexyl iodide and neopentyl iodide.

Following the procedure outlined above, the effect of chain branching on guard bed performance was investigated by comparing removal of hexyl iodide with removal of neopentyl iodide (Example F). Results appear in FIG. 5.

Examples 2–4

Figure 6:
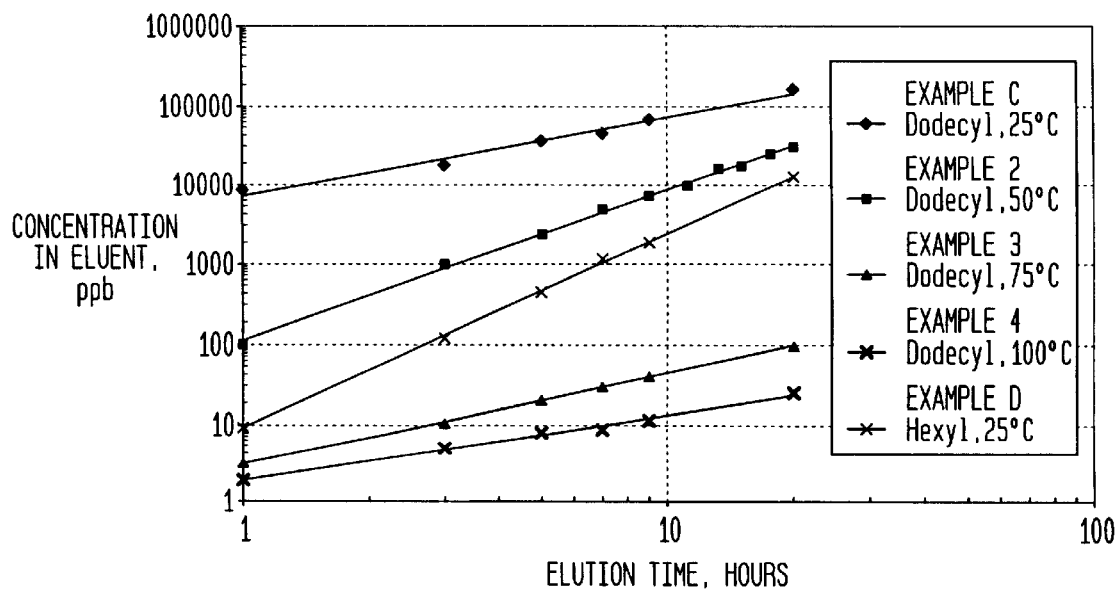
FIG. 6 is a plot of various elution isotherms at 25° C. to 100° C. for alkyl iodide removal from acetic acid.

Following the procedure outlined above, performance of a silver-exchanged Amberlyst® 15 guard bed was evaluated for removal of dodecyl iodide at 25° C., 50° C., 75° C., and 100° C. and for removal of hexyl iodide at 25° C. Results appear in FIG. 6 where Examples C and D also appear for purposes of comparison. Here again, it can be seen removal efficiencies in useful capacities of the bed are greatly enhanced at temperatures above about 50° C.

Example 5

Figure 7:
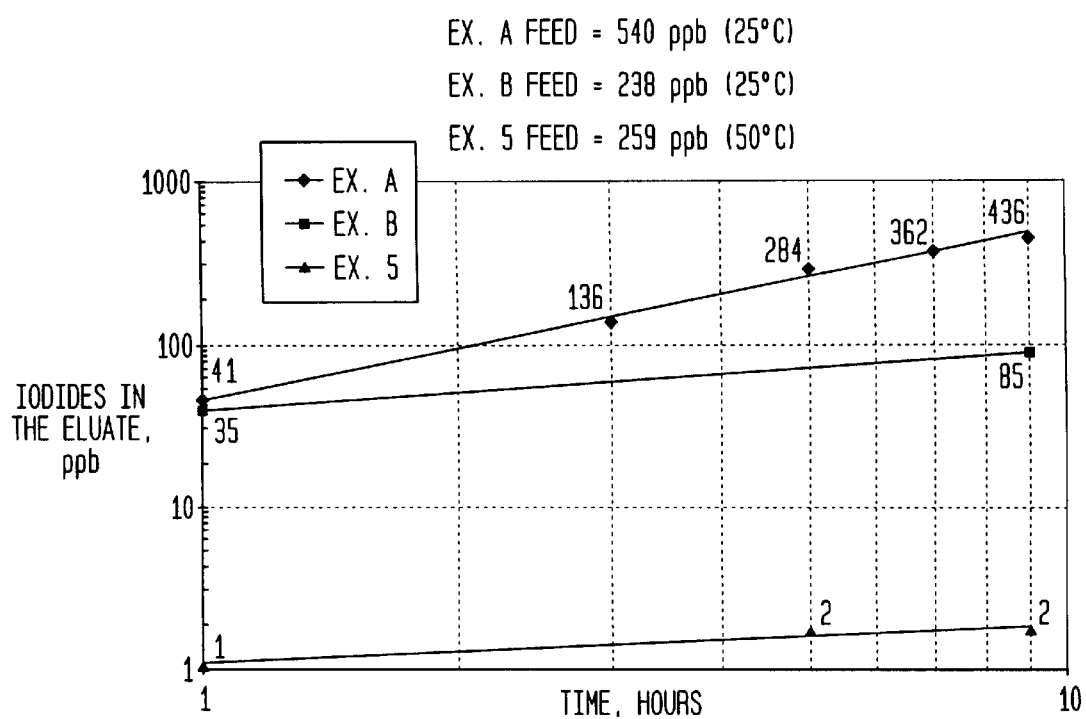
FIG. 7 is a plot of iodide concentration in acetic acid eluent vs. time for commercial samples of material treated at 25° C. and at 50° C. in accordance with the present invention.

Following the procedures outlined above, samples of acetic acid (drying column residue) from a Monsanto type acetic acid plant containing respectively 540 ppb total iodide (Example A), 238 ppb total iodide (Example B) and 259 ppb total iodide (Example 5). The acid was treated, as before, using a silver exchanged Amberlyst® 15 guard bed at 25° C. and 50° C. As can be seen from FIG. 7, performance at 50° C. was far superior to removal efficiencies at 25° C. Indeed the guard bed removed greater than 99% (nearly quantitative removal) of the total iodide at 50° C.

As part of the present invention it is desirable to control the amount of acetaldehyde carbonyl impurities that are included in the product stream. Some techniques involve the treatment of acetic acid with oxidizers, ozone, water, methanol, amines and the like. These techniques might include, for example, the removal of carbonyl impurities from organic streams by treating the organic stream with an amine compound such as hydroxylamine which reacts with the carbonyl compounds to form oximes followed by distillation to separate the purified organic product from the oxime reaction products. As noted above, this method adds cost to the process.

There is disclosed in U.S. Pat. No. 5,625,095 to Miura et al. and PCT International Application No. PCTIUS 97/18711 Publication No. WO98/17619 various methods of removing aldehydes and other impurities from a rhodium catalyzed acetic acid production process. Generally these methods involve extracting undesirable impurities from the process recycle streams to reduce acetaldehyde concentrations in the system. The disclosure of the '095 patent and International Application No. PCT/US97/18711 are hereby incorporated into this application by reference and these techniques may be used to control the acetaldehyde concentration in the system of the present invention.

Another method is to control the acetaldehyde concentration in the product stream by minimizing the production of byproducts. It has been discovered that by maintaining the hydrogen partial pressures at or below levels previously recognized in the art is beneficial. The production of acid aldehyde and its derivatives, particularly crotonaldehyde and 2-ethyl crotonaldehyde can be dramatically reduced. The following examples illustrate this feature which can be employed in connection with the present invention.

A reaction system which is employed, wherein the present improvement is demonstrated, comprises (a) a liquid-phase homogeneous carbonylation reactor, (b) a so-called "flasher", and (c) a "methyl iodide-acetic acid splitter column". The carbonylation reactor is typically a stirred autoclave within which the reacting liquid contents are maintained automatically at a constant level. Into this reactor there are continuously introduced fresh methanol, sufficient water to maintain at least a finite concentration of water in the reaction medium, recycled catalyst solution from the flasher base, and recycled methyl iodide and methyl acetate from the overhead of the methyl iodide-acetic acid splitter column. Alternate distillation systems can be employed so long as they provide means for recovering the crude acetic acid and recycling to the reactor catalyst solution, methyl iodide, and methyl acetate. In the process, a mixed carbon monoxide/hydrogen feed is continuously introduced into the carbonylation reactor just below the agitator which is used to stir the contents. The mixed gaseous feed is, of course, thoroughly dispersed through the reacting liquid by this means. A gaseous purge stream is vented from the reactor to prevent buildup of gaseous by-products and to maintain a set carbon monoxide partial pressure at a given total reactor pressure. By controlling the venting of gases, it is also possible to control the hydrogen partial pressure in the reactor. The temperature of the reactor is controlled automatically, and the carbon monoxide/hydrogen feed is introduced at a rate sufficient to maintain the desired total reactor pressure.

Liquid product is drawn off from the carbonylation reactor at a rate sufficient to maintain a constant level therein and is introduced to the flasher at a point intermediate between the top and bottom thereof. In the flasher the catalyst solution is withdrawn as a base stream (predominantly acetic acid containing the rhodium and the iodide salt along with lesser quantities of methyl acetate, methyl iodide, and water), while the overhead of the flasher comprises largely the product acetic acid along with methyl iodide, methyl acetate, and water. A portion of the carbon monoxide and hydrogen along with gaseous by-products such as methane, hydrogen, and carbon dioxide exits the top of the flasher.

The product acetic acid drawn from the base of the methyl iodide-acetic acid splitter column (it can also be withdrawn as a side stream near the base) is then drawn off for final purification as desired by methods well known in the art and which are outside the scope of the present invention. The overhead from the methyl iodide-acetic acid splitter, comprising mainly methyl iodide and methyl acetate, is recycled to the carbonylation reactor.

The primary reaction control method comprises continually analyzing the liquid contents of the reactor as well as the carbon monoxide and hydrogen content of the gas in the reactor vent and, on the basis of these analyses, controlling the flow of carbon monoxide, hydrogen, water, methanol, and methyl iodide to maintain the specified reaction medium composition. It should be further explained that the methanol addition to the carbonylation reactor is based not on an analysis of its contents for methanol but, rather, on analysis for methyl acetate content. Most of the methanol is converted almost immediately to methyl acetate when it enters the carbonylation reactor.

In a continuous process which is described above, the catalyst system is maintained, with the reactants being continuously supplied to the reaction zone containing the catalyst system at the desired temperature and pressure. The products are continuously withdrawn, as described above by withdrawing a portion of the solution containing the catalyst system, unreacted feed, equilibrium components, and the desired product. The desired product is then separated from such solution to permit recycling of the catalyst containing solution which includes unreacted feed and also equilibrium components.

The following examples are included to demonstrate methods of controlling the level of aldehyde impurities in accordance with the present invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Examples 6–9

A continuous pilot plant equipped generally as described above with a 4-liter reactor operating at 1.5 liter reaction volume was used to investigate the effect of hydrogen partial pressure on the formation of by-products while carbonylating methanol. Operating conditions and results appear in Table 2 below. "Column Residue Impurities" refers to impurities in the crude acetic acid product and "H2pp" refers to the partial pressure of hydrogen in the reaction vessel in pounds per square inch absolute.

TABLE 2

| Hydrogen Partial Pressure Data | | | | |
|---|---|---|---|---|
| Examples | 6 | 7 | 8 | 9 |
| Reactor H2pp (psia) | 2.0 | 3.3 | 9.4 | 14.6 |
| Methanol Feed (grams/min) | 14.9 | 15.0 | 15.0 | 15.0 |
| Reactor Composition | | | | |
| Methyl Iodide, wt % | 10.6 | 11.0 | 10.8 | 10.9 |
| Methyl Acetate, wt % | 2.6 | 2.5 | 2.5 | 2.5 |
| Water, wt % | 4.0 | 4.0 | 4.1 | 4.3 |
| Rh, ppm | 631 | 652 | 657 | 651 |
| LiI, wt % | 6.6 | 8.2 | 8.4 | 8.7 |
| Rx. Temp. deg C. | 195.2 | 194.0 | 191.8 | 192.3 |
| Column Residue Impurities | | | | |
| Propionic Acid, ppm | 140 | 197 | 363 | 500 |
| Crotonaldehyde, ppm | 1 | 4 | 6 | 8 |

TABLE 2-continued

Hydrogen Partial Pressure Data

| Examples | 6 | 7 | 8 | 9 |
|---|---|---|---|---|
| 2-ethyl-Crotonaldehyde, ppm | 1 | 3 | 6 | 8 |
| Butyl Acetate, ppm | 3 | 6 | 13 | 16 |

As can be seen, the impurity profile is improved at lower hydrogen partial pressures in the reactor.

While the foregoing examples demonstrate the reduction of crotonaldehyde and the like, it will be appreciated by one of skill in the art that other impurities and byproducts in rhodium catalyzed carbonylation systems include butane, butanol, butyl acetate, butyl iodide, ethanol, ethyl acetate, ethyl iodide, hexyl iodide and high boiling impurities. The present invention appears to minimize production of these impurities as well.

Another method of controlling the acid aldehyde involves operating the process at relatively low concentrations of methyl iodide.

A typical homogeneous reaction system which is employed for the following examples is generally as described above and comprises (a) a liquid-phase carbonylation reactor, (b) a flasher, and (c) a methyl iodide-acetic acid splitter column. The carbonylation reactor is typically a stirred autoclave within which the reacting liquid contents are maintained automatically at a constant level. Into this reactor there are continuously introduced fresh methanol, sufficient water to maintain at least a finite (>50 ppm and preferably at least about 0.1 wt %) concentration of water in the reaction medium, recycled catalyst solution from the flasher base, and recycled methyl iodide, methyl acetate and water from the overhead of the methyl iodide-acetic acid splitter column. A distillation system can be employed to further process the condensed overhead stream from the flasher. The residue from the flasher is recirculated to the reactor. Carbon monoxide is continuously introduced into and thoroughly dispersed within the carbonylation reactor. A gaseous purge stream is vented from the head of the reactor to prevent buildup of gaseous by-product and to maintain a set carbon monoxide partial pressure at a given total reactor pressure. The temperature and pressure of the reactor are controlled by methods known in the art.

Crude liquid product is drawn off from the carbonylation reactor at a rate sufficient to maintain a constant level therein and is introduced to the flasher at a point intermediate between the top and bottom thereof. In the flasher the catalyst solution is withdrawn as a base stream predominantly acetic acid containing the rhodium catalyst and the iodide salt along with lesser quantities of methyl acetate, methyl iodide, and water, while the condensed overhead of the flasher comprises largely the crude product, acetic acid, along with methyl iodide, methyl acetate, and water. A portion of the carbon monoxide along with gaseous by-products such as methane, hydrogen, and carbon dioxide exits the top of the flasher.

The dry acetic acid (<1500 ppm water) product is drawn from the base of the methyl iodide-acetic acid splitter column (it can also be withdrawn as a side stream near the base) for final purification as desired by methods which are obvious to those skilled in the art and which are outside the scope of the present inventions. The overhead from the methyl iodide-acetic acid splitter, comprising mainly methyl iodide, methyl acetate and water, is recycled to the carbonylation reactor.

The following specific examples are supplied for the purpose of better illustrating the invention. These examples are not intended, however, to limit or restrict the scope of the invention in any way and should not be construed as providing conditions, parameters, or values which must be utilized exclusively in order to practice the present invention.

Examples 10–12

Continuous methanol carbonylations were performed in a reaction system as described above, which includes a stirred reactor, a flasher, and a methyl iodide-acetic acid splitter column. Except for varying methyl iodide concentration the reaction conditions were repeated in each of the following examples so as to demonstrate the effect of reduced methyl iodide on acetaldehyde.

Each run achieved steady state conditions before collecting impurity data by operating the reactor continuously to maintain constant target reaction compositions and conditions, as indicated in Table 3. Then, for at least 12 hours thereafter, data was collected and plots were maintained to indicate that the carbonylation reaction was in steady state mode.

The results of Examples 10–12 are provided in Table 3. With respect to Table 3, the values are mass balance data taken over at least a 12 hour period at steady state conditions. The results of Examples 10 and 12 each represent a single mass balance run. The results of Example 11 are an average of two mass balance operating periods.

TABLE 3

Continuous Operation Results

|  | 10 | 11 | 12 |
|---|---|---|---|
| REACTION CONDITIONS |  |  |  |
| LiI (wt %) | 10 | 10 | 10 |
| Rh (ppm) | 630 | 610 | 620 |
| Water (wt %) | 4.0 | 4.1 | 3.9 |
| Methyl Acetate (wt %) | 3.0 | 2.7 | 3.0 |
| Methyl Iodide (wt %) | 2.0 | 3.5 | 6.7 |
| Hydrogen Partial Pressure (psia) | 12 | 11 | 11 |
| Acetic Acid STY (moI/L-hr) | 7 | 11 | 16 |
| REACTOR CONCENTRATION |  |  |  |
| Acetaldehyde (ppm) | 540 | 610 | 660 |

As can be seen, the acetaledehyde concentration in the reactor is reduced with a reduction of MEI.

In a still further aspect of the invention, there is provided a method of reducing the Color Value (Pt—Co) units of acetic acid, hereafter referred to as APHA Color Value.

Typically, this method involves treating acetic acid to achieve a consistently low level of below about 5 APHA color units. To illustrate, 10 samples of acetic acid were examined at various levels of iodide and color impurities. Only one sample, which was derived from material having an APHA Color Value of 65, exhibited a value of greater than 5 APHA color units after treatment. This aspect of the present invention is better appreciated from the Examples.

Examples 13–22

A resin bed was prepared utilizing Rohm & Haas Amberlyst® 15 macroporous resin with 10% of the sites converted to the silver (Ag+) form. Acetic acid was obtained from the drying column residue of a Monsanto-type plant (e.g., line 64 of FIG. 2) and from a residue stream of a heavy ends column from a Monsanto-type acetic acid plant. As will be appreciated by one of skill in the art, the heavy ends has a higher concentration of iodide and color impurities of generally the same type present in the drying column residue, that is, including decyl iodide and dodecyl iodide. The drying column residue and drying column residue spiked with 0.1% heavy ends residue was treated by contracting it with the resin prepared as above at 50° C. as further detailed in Table 4 below. As used herein, "Color Value", "Pt—Co Color Units", "Color Units", and like terminology refer to APHA, sometimes referred to as Hazen Pt—Co color units determined in accordance with ASTM test method designation D1209–62 "Standard Method of Test for Color of Clear Liquids Using Platinum-Cobalt Color Standards", preferably utilizing a suitable spectrometer.

TABLE 4

Color Reduction for Acetic Acid

|  | Total Iodide (ppb) | Color Value (Pt-Co units) |
|---|---|---|
| Initial Drying column residue material | 197 | 5.6 |
| Drying column res. +0.1% heavy ends (for accelerated exhaustion tests) | 728 | 65 |
| Resin bed outlet product after continuous feeding of Drying column residue +0.1% heavy ends for: | | |
| Feed | 728.0 | 65.0 |
| 4 hours | 12.3 | 4.6 |
| 9 hours | 13.4 | 4.5 |
| 14 hours | 3.6 | 5.6 |
| 20 hours | 4.6 | 4.8 |
| 20.3 hours | 8.1 | 4.5 |
| average | 8.4 | 4.8 |
| Resin bed outlet product after continuing feed with drying column Residue without heavy ends: | | |
| Continuing with new feed | 197.0 | 5.6 |
| 30 hours | 5.3 | 4.4 |
| 36 hours | 2.0 | 4.4 |
| 41 hours | 8.3 | 4.2 |
| average | 5.2 | 4.3 |

Resin bed = Rohm & Haas Amberlyst ® 15 with 10% sites in the Ag+ form.
Continuous operating conditions:
Feed rate = 4 to 5 Bed Volumes/hour
Bed Temperature = 75 degrees C.
Addition of 0.1% heavy ends to the Drying column residue feed material was used to accelerate the exhaustion of the resin by increasing the concentration of the same iodide and color body species already present in the stream.

As can be seen, treatment with the resin particularly at elevated temperatures is effective to maintain the Color Value at a level of less than 10 and usually less than 5 Pt—Co Color Units. The treatment is particularly useful in connection with a continuous process for producing acetic acid comprising: (a) reacting methanol with a carbon monoxide feedstock in a carbonylation reactor holding a catalytic reaction medium while maintaining in the reaction medium during the course of the reaction at least a finite concentration of from about 0.1 weight percent up to less than 14 weight percent of water; (b) withdrawing a stream of the reaction medium from the reactor and vaporizing a portion of the withdrawn medium in a flashing step; (c) distilling the flashed vapor to form a liquid acetic acid product stream utilizing in a primary purification train up to two distillation columns while providing one or more recycle streams to said reactor; and (d) removing iodides from said liquid acetic acid product stream and simultaneously controlling the Color Value of said acetic acid stream such that the product has an iodide content of less than about 10 ppb iodide and a Color Value of less than about 10, preferably less than about 5, wherein said step of removing iodides and controlling the Color Value of said product stream consists essentially of contacting said liquid acetic acid product stream with a silver or a mercury exchanged ion exchange substrate at a temperature of at least about 50° C. wherein at least one percent of the active sites of said resin have been converted to the silver or mercury form.

The method of treating the acetic acid stream is typically applied to a stream having a Color Value of greater than about 5 and includes contacting the liquid acetic acid product stream with a silver or a mercury exchanged ion exchange substrate at a temperature of at least about 50° C. wherein at least one percent of the active sites of said resin have been converted to the silver or mercury form such that the treated acetic acid has a Color Value of less than about 5 after treatment. Sometimes the acetic acid has a Color Value of greater than about 10 prior to contacting the stream with said silver or mercury exchanged ion exchange substrate. Typically, the acetic acid stream contains decyl iodides and dodecyl iodides prior to treatment with said silver or mercury exchanged ion exchange substrate.

While the invention has been described in detail here and above various modifications to specific embodiments within the spirit and scope of the present invention will be readily apparent to those of skill in the art. The present invention is defined in the appended claims.

What is claimed is:

1. A continuous process for producing acetic acid comprising:
   (a) reacting methanol with a carbon monoxide feedstock in a carbonylation reactor holding a catalytic reaction medium while maintaining in said reaction medium during the course of said reaction at least a finite concentration of from about 0.1 weight percent up to less than 14 weight percent of water;
   (b) withdrawing a stream of said reaction medium from said reactor and vaporizing a portion of said withdrawn medium in a flashing step;
   (c) distilling the flashed vapor to form a liquid acetic acid product stream utilizing in a primary purification train up to two distillation columns while providing one or more recycle streams to said reactor; and
   (d) removing iodides from said liquid acetic acid product stream and simultaneously controlling the Color Value of said acetic acid stream such that the product has an iodide content of less than about 10 ppb iodide and a Color Value of less than about 10, wherein said step of removing iodides and controlling the Color Value of said product stream consists essentially of contacting said liquid acetic acid product stream with a silver or a mercury exchanged ion exchange substrate at a temperature of at least about 50° C. wherein at least one percent of the active sites of said resin have been converted to the silver or mercury form.

2. A method of treating an acetic acid stream having a Color Value of greater than about 10 comprising contacting said liquid acetic acid product stream with a silver or a mercury exchanged ion exchange substrate at a temperature of at least about 50° C. wherein at least one percent of the active sites of said resin have been converted to the silver or mercury form such that the treated acetic acid has a Color Value of less than about 10 after treatment.

3. The method according to claim 2, wherein said acetic acid has a Color Value of greater than about 5 prior to contacting said stream with said silver or mercury exchanged ion exchange substrate, and a Color Value of less than about 5 after such treatment.

4. The method according to claim 3, wherein said acetic acid stream contains decyl iodides and dodecyl iodides prior to contacting said stream with said silver or mercury exchanged ion exchange substrate.

5. A continuous process for producing acetic acid comprising:
 (a) reacting methanol with a carbon monoxide feedstock in a carbonylation reactor holding a catalytic reaction medium while maintaining in said reaction medium during the course of said reaction at least a finite concentration of from about 0.1 weight percent up to less than 14 weight percent of water together with (i) a salt soluble in the reaction medium at the reaction temperature in an amount operative to maintain a concentration of ionic iodide in the range of from about 2 to about 20 weight percent effective as a catalyst stabilizer and co-promoter, (ii) from about 1 to 20 weight percent methyl iodide, (iii) from about 0.5 to about 30 weight percent methyl acetate; (iv) a rhodium catalyst, and (v) acetic acid;
 (b) withdrawing a stream of said reaction medium from said reactor and vaporizing a portion of said withdrawn medium in a flashing step;
 (c) distilling the flashed vapor to form a liquid acetic acid product stream utilizing in a primary purification train up to two distillation columns while providing one or more recycle streams to said reactor; and
 (d) removing iodides from said liquid acetic acid product stream such that the product has an iodide content of less than about 10 ppb iodide, wherein said step of removing iodides from the acetic acid product stream is selected from the group consisting of (i) contacting said liquid acetic acid product stream with an anionic ion exchange resin at a temperature of at least about 100° C. followed by contacting said liquid acetic acid product stream with a silver or mercury exchanged ion exchange substrate wherein at least 1 percent of the active sites of said resin have been converted to the silver or mercury form or (ii) contacting said liquid acetic acid product stream with a silver or a mercury exchanged ion exchange substrate at a temperature of at least about 50° C. wherein at least one percent of the active sites of said resin have been converted to the silver or mercury form, and further comprising controlling the level of aldehyde impurities in said product stream by removing aldehydes from said recycle stream.

6. The process according to claim 5, wherein said aldehydes are removed from a recycle stream by distillation.

7. A continuous process for producing acetic acid comprising:
 (a) reacting methanol with a carbon monoxide feedatock in a carbonylation reactor holding a catalytic reaction medium while maintaining in said reaction medium during the course of said reaction at least a finite concentration of from about 0.1 weight percent up to less than 14 weight percent of water together with (i) a salt soluble in the reaction medium at the reaction temperature in an amount operative to maintain a concentration of ionic iodide in the range of from about 2 to about 20 weight percent effective as a catalyst stabilizer and co-promoter, (ii) from about 1 to 20 weight percent methyl iodide, (iii) from about 0.5 to about 30 weight percent methyl acetate; (iv) a rhodium catalyst, and (v) acetic acid;
 (b) withdrawing a stream of said reaction medium from said reactor and vaporizing a portion of said withdrawn medium in a flashing step;
 (c) distilling the flashed vapor to form a liquid acetic acid product stream utilizing in a primary purification train up to two distillation columns while providing one or more recycle streams to said reactor; and
 (d) removing iodides from said liquid acetic acid product stream such that the product has an iodide content of less than about 10 ppb iodide, wherein said step of removing iodides from the acetic acid product stream is selected from the group consisting of (i) contacting said liquid acetic acid product stream with an anionic ion exchange resin at a temperature of at least about 100° C. followed by contacting said liquid acetic acid product stream with a silver or mercury exchanged ion exchange substrate wherein at least 1 percent of the active sites of said resin have been converted to the silver or mercury form or (ii) contacting said liquid acetic acid product stream with a silver or a mercury exchanged ion exchange substrate at a temperature of at least about 50° C. wherein at least one percent of the active sites of said resin have been converted to the silver or mercury form, and further comprising controlling the level of aldehyde impurities in said product stream by maintaining in said reactor a methyl iodide concentration of about 5 weight percent or less.

8. The method according to claim 7, wherein the level of methyl iodide in said reactor is maintained at a level of from about 1 to about 5 weight percent.

9. A continuous process for producing acetic acid comprising:
 (a) reacting methanol with a carbon monoxide feedstock in a carbonylation reactor holding a catalytic reaction medium while maintaining in said reaction medium during the course of said reaction at least a finite concentration of from about 0.1 weight percent up to less than 14 weight percent of water together with (i) a salt soluble in the reaction medium at the reaction temperature in an amount operative to maintain a concentration of ionic iodide in the range of from about 2 to about 20 weight percent effective as a catalyst stabilizer and co-promoter, (ii) from about 1 to 20 weight percent methyl iodide, (iii) from about 0.5 to about 30 weight percent methyl acetate; (iv) a rhodium catalyst, and (v) acetic acid;
 (b) withdrawing a stream of said reaction medium from said reactor and vaporizing a portion of said withdrawn medium in a flashing step;
 (c) distilling the flashed vapor to form a liquid acetic acid product stream utilizing up to two distillation columns while providing one or more recycle streams to said reactor;
 (d) controlling the level of iodide impurities in said product stream by maintaining a hydrogen partial pressure of less than about 6 psia in the reactor at a total pressure of from about 15 to 40 atmospheres in the reactor; and
 (e) removing iodides from said liquid acetic acid product stream such that the product has an iodide content of less than about 10 ppm iodide by contacting said liquid acetic acid product stream with a silver or mercury exchanged ion exchanged substrate at a temperature of the product stream of greater than about 50° C., and wherein said product stream contains organic iodide with an aliphatic chain length of C10 or greater.

10. The method according to claim 9, wherein said product stream contains organic iodides, at least about 25% have an aliphatic chain length of C10 or greater.

11. The method according to claim 10, wherein at least about 50% of the organic iodide in said organic media comprise organic iodides having an aliphatic chain length of C10 or greater.

12. The method according to claim 9, wherein said organic iodides comprise iodides selected from the group consisting of decyl iodide (C10) and dodecyl (C 12) iodide.

13. The method according to claim 12, wherein said treatment is effective to remove at least about 90% of the decyl (C10) and dodecyl (C12) iodides from the organic medium.

14. The process according to claim 5, wherein said step of removing iodides from said liquid acetic acid product stream comprises contacting said liquid acetic acid product stream with a polyvinylpyridine resin.

15. The process according to claim 14, wherein said step of contacting said acetic acid product stream with said polyvinylpyridine resin is carried out a temperature of at least about 150° C.

16. The method according to claim 5, wherein said step of removing iodides from said liquid acetic acid product stream comprises contacting said liquid acetic acid product stream with a polyvinylpyrrolidone resin.

17. The method according to claim 16, wherein said step of contacting said liquid acetic acid product residue stream with said polyvinylpyrrolidone resin is carried out a temperature of at least about 150° C.

18. The process according to claim 5, wherein said step of removing iodides from said liquid acetic acid product stream comprises contacting said product stream with a macroreticular, silver or mercury exchanged ion exchange resin wherein at least 1% of the active sites have been converted to the silver or mercury form at a temperature at least about 50° C.

19. The process according to claim 5, wherein said step of removing iodides from said liquid acetic acid product stream comprises contacting said product stream with a macroreticular, silver or mercury exchanged ion exchange resin wherein at least 1% of the active sites have been converted to the silver or mercury form at a temperature at least about 60° C.

20. The process according to claim 19, wherein said liquid acetic acid product stream is contacted with said silver or mercury exchanged macroreticular resin at a temperature of at least about 70° C.

21. The process according to claim 18, wherein from about 25 to about 75% of the active site of said macroreticular resin have been converted to the silver form.

22. The process according to claim 21, wherein about 50% of the active sites of said macroreticular resin have been converted to the silver form.

23. The method to claim 9, wherein said product stream has from about 10 to about 1000 ppb total iodides prior to treatment with said silver or mercury exchanged cationic ion exchange substrate.

24. The method according to claim 23, wherein said non-aqueous organic media contains from about 20 to about 750 ppb total iodides prior to treatment with said silver or mercury exchanged cationic ion exchange substrate.

25. The method according to claim 24, wherein said treatment of contacting said organic media with said silver or mercury exchanged cationic ion exchange substrate at a temperature greater than about 50° C. is effective to remove at least about 99% of the total iodide present in said organic media.

26. The method according to claim 9, wherein said ion exchange substrate is a sulfonic acid functionalized resin.

27. The method according to claim 9, wherein said stream, prior to contacting said ion exchange substrate, has an iodide content of greater than about 100 ppb organic iodide.

28. The method according to claim 27, said stream, after contacting said ion exchange substrate, has an organic iodide content of less than 10 ppb.

* * * * *